United States Patent
Belcaro et al.

(10) Patent No.: US 9,308,230 B2
(45) Date of Patent: Apr. 12, 2016

(54) COMBINATION OF PROANTHOCYANIDINS AND CENTELLA ASIATICA FOR THE TREATMENT OF ATHEROSCLEROSIS

(75) Inventors: Gianni Belcaro, Pescara (IT); Carolina Burki, Geneva (CH); Victor Ferrari, Geneva (CH)

(73) Assignee: HORPHAG RESEARCH IP, Limassol (CY)

( * ) Notice: Subject to any disclaimer, the term of this patent is extended or adjusted under 35 U.S.C. 154(b) by 175 days.

(21) Appl. No.: 13/390,118

(22) PCT Filed: Aug. 11, 2010

(86) PCT No.: PCT/IB2010/053637
§ 371 (c)(1),
(2), (4) Date: Mar. 12, 2012

(87) PCT Pub. No.: WO2011/018763
PCT Pub. Date: Feb. 17, 2011

(65) Prior Publication Data
US 2012/0164244 A1 Jun. 28, 2012

(30) Foreign Application Priority Data
Aug. 12, 2009 (WO) .................. PCT/IB2009/006525

(51) Int. Cl.
*A61K 36/736* (2006.01)
*A61K 36/15* (2006.01)
*A61K 31/353* (2006.01)
*A61K 36/185* (2006.01)
*A61K 36/23* (2006.01)
*A61K 36/48* (2006.01)
*A61K 36/52* (2006.01)
*A61K 36/734* (2006.01)
*A61K 36/82* (2006.01)
*A61K 36/87* (2006.01)

(52) U.S. Cl.
CPC ............... *A61K 36/15* (2013.01); *A61K 31/353* (2013.01); *A61K 36/185* (2013.01); *A61K 36/23* (2013.01); *A61K 36/48* (2013.01); *A61K 36/52* (2013.01); *A61K 36/734* (2013.01); *A61K 36/736* (2013.01); *A61K 36/82* (2013.01); *A61K 36/87* (2013.01)

(58) Field of Classification Search
None
See application file for complete search history.

(56) References Cited

U.S. PATENT DOCUMENTS 7,241,461 B2 * 7/2007 Myhill et al. .................. 424/729

FOREIGN PATENT DOCUMENTS

| BE | 897965 A | * | 1/1984 |
| EP | 1523894 A1 | | 4/2005 |
| JP | 2002238497 A | | 8/2002 |
| JP | 2005237203 A | * | 9/2005 |
| JP | 2007008817 A | * | 1/2007 |
| KR | 100846292 B1 | | 7/2008 |
| WO | WO-03080062 A1 | | 10/2003 |

OTHER PUBLICATIONS

Translation of JP 2005237203 A to Ono et al. Publication date: Sep. 2005.*
Translation of JP 200700817 A to Takumi et al. Publication date: Jan. 2007.*
Translation of Abstract of BE 897965 A to Lab Bago SA. Publication date: Jan. 1984.*
"What is Atherosclerosis". NIH: National Heart, Lungs and Blood Institute. Retrieved from the Internet on: Oct. 29, 2013. Retrieved from: <URL: http://www.nhlbi.nih.gov/health/health-topics/topics/atherosclerosis/>.*
Pycnogenol®. Internet Date: Jul. 13, 2009. Section referenced: Passwater (1991). [Retrieved from the Internet on: Oct. 29, 2013]. Retrieved from: <URL: http://www.naturalfactors.com/Frontend/WebsiteImages/naturalfactorscanada/documents/452_Pycnog-RS.pdf.pdf>.*
Science News. "Aspirin and Atherosclerosis: Mechanism Uncovered". Sep. 25, 2008 [Retrieved from the Internet on: Oct. 29, 2013]. Retrieved from: <URL: http://www.sciencedaily.com/releases/2008/09/080922155916.htm>.*
Database WPI, Week 200304, Thomson Scientific, London, GB; AN 2003-042530 XP002578473.
Abascal K et al., "Botanicals for chronic venous insufficiency", Alternative and Complementary Therapies 20071201 US LNKD-DOI:10.1089/ACT.2007.13609, vol. 13, No. 6, Dec. 1, 2007, pp. 304-311, XP002579500, ISSN: 1076-2809, table 2 p. 309, left-hand column, paragraph 1—right-hand column, paragraph 1, p. 310, left-hand column, paragraph 2, abstract.
Ramelet A A et al., "Veno-active drugs in the management of chronic venous disease. An international consensus statement: Current medical position, prospective views and final resolution", Clinical Hemorheology and Microcirculation 2005 NL, vol. 33, No. 4, 2005, pp. 309-319, XP9132315, ISSN: 1386-0291, tables 2, 4.
Database WPI, Week 200965, Thomson Scientific, London, GB; AN 2009-E18421 XP002578465.
Jun Yamakoshi, et al., "Proanthocyanidin-rich extract from grape seeds attenuates the development of aortic atherosclerosis in cholesterol-fed rabbits," *Atherosclerosis*, vol. 142, pp. 139-149 (1999).
L. Incandela, et al., "Modification of the Echogenicity of Femoral Plaques After Treatment with Total Triterpenic Fraction of *Centella asiatica*: A Prospective, Randomized, Placebo-Controlled Trial," *Angiology*, vol. 52, Supplement 2, pp. 569-573 (2001).

* cited by examiner

*Primary Examiner* — Amy L Clark
(74) *Attorney, Agent, or Firm* — Oliff PLC

(57) ABSTRACT

The invention relates to a preparation for medical purposes and more specifically to a preparation consisting of the combination of proanthocyanidins such as Pycnogenol or grape seeds and *Centella asiatica* and/or extracts thereof, for use in the prevention or treatment of atherosclerosis.

12 Claims, No Drawings

COMBINATION OF PROANTHOCYANIDINS AND CENTELLA ASIATICA FOR THE TREATMENT OF ATHEROSCLEROSIS

FIELD OF THE INVENTION

The invention relates to preparations for medical purposes and more specifically to a preparation consisting of the combination of proanthocyanidins such as Pycnogenol or grape seeds and *Centella asiatica* and/or extracts thereof, for use in the prevention or treatment of atherosclerosis.

BACKGROUND OF THE INVENTION

Diseases affecting the heart are commonly classified under the term heart diseases. More particularly, cardiovascular diseases refer to the class of heart diseases that involve the heart and the blood vessels (arteries and veins). One type of cardiovascular diseases is atherosclerosis. Atherosclerosis is a syndrome affecting arterial blood vessels which carry oxygen-rich blood to the heart and other parts of the body. It concerns the process in which deposits of fatty substances, cholesterol, cellular waste products, calcium and other substances build up in the inner lining of arteries and form hard substances called plaque. It usually affects large and medium-sized arteries.

Studies show that atherosclerosis is a slow, complex disease that typically starts in childhood and often progress when people become older. Over time, plaques can grow large enough to significantly reduce the blood's flow through arteries that produce a diminution of oxygen-rich blood to organs. Most of the damage occurs when plaques become fragile and break (rupture). Plaques that break cause blood clots blocking the blood flow or travelling to another part of the body. When a blood vessel that feeds the heart is blocked, it causes a heart attack. If it blocks a blood vessel that feeds the brain, it causes a stroke. And if blood supply to the arms or legs is reduced, it can cause difficulties in moving and eventually gangrene.

Certain conditions or habits may increase the events of developing atherosclerosis. These conditions (high blood cholesterol, especially LDL, smoking and exposure to tobacco smoke, high blood pressure, diabetes, obesity, physical inactivity . . . ) are known as risk factors. Changes in lifestyle and/or taking medicines to treat some particular risk factors can often reduce the genetic influences and prevent from atherosclerosis.

As mentioned above, atherosclerosis is a syndrome which affects people from childhood and progress with age. For centuries, medicine tries to find appropriate treatments to prevent and/or minimize the risks of atherosclerosis. Some attempts have been done with the compositions containing proanthocyanidins (such as Pycnogenol®).

WO 2007/084648 (Mars, Inc.) discloses compositions containing mixed 4 to 6 procyanidin dimers and certain derivatives thereof, for inducing vasodilation, treating or preventing diseases or disorders of the vascular system (e.g. hypertension, cardiovascular disease, stroke), and/or treating or preventing NO-responsive conditions or diseases. The disclosed compositions may be used as a pharmaceutical, a food, a food additive, or a dietary supplement. The composition may optionally contain an additional therapeutic or beneficial-to-health agent, or may be administered in combination with another therapeutic or beneficial-to-health agent.

Abascal K et al. "Botanicals for chronic venous insufficiency" ALTERNATIVE AND COMPLEMENTARY THERAPIES, Vol. 13, No 6, December 2007, pp 304-311; also discloses botanicals that are useful as adjunctive therapy for the treatment of chronic venous insufficiency (CVI). Botanicals used include *Ruscus aculeatus*, horse chestnut seed, *Centella asiatica*, *Vitis vinifera* and oligomeric proanthocyanidins such as Pycnogenol®.

Ramelet A et al. "Veno-active drugs in the management of chronic venous disease. An international consensus statement: Current medical position, prospective views and final resolution" CLINICAL HEMORHEOLOGY AND MICROCIRCULATION, Vol. 33, N° 4, 2005, pp 309-319; discloses veno-active drugs (VAD) having effects on edema and symptoms related to chronic venous disease (CVD) especially venous pain. This review has classified various VAD and the level of Evidence-Based Medicine (EBM) of each drug has been determined Pycnogenol® and *Centella asiatica* are been classified under Grade C as showing less well demonstrated effects on chronic venous disease.

WO 2007/133981 (RATH Matthias et al.) discloses biochemical compositions effective in the prevention and treatment resulting from the inhibition of an atherogenic process, comprising ascorbic acid, lysine, magnesium, cysteine, pyridoxine HCL, riboflavin, folic acid, cyanocobalamin vitamin B12, S-Adenosyi-L-Methionine, choline bitartrafe, copper glycinate, epigalocatechin gallate, quercetin, asiatic acid, and Pycnogenol®. More precisely the disclosed compositions act on the growth of smooth muscle cell and the invasion of extracellular matrix by smooth muscle cell. The compositions may be administered orally, intravenously, or parenterally.

Other documents cite some possible associations of plant extract among big lists of compounds. For example EP 1 523 894 (Cognis Iberia S.L.) discloses a preparation containing extracts from the plant *centella asiatica* or the active component (component a). Plant extracts contained, include *camellia sinensis, pinia silvestris, vitis vinifera, litchi chinensis, potentilla errecta* and their mixtures. Components a and b or c are in the mass ratio 90:10 to 10:90. The preparation is encapsulated.

JP 2002 238497 A (Fankeru KK), XP002578473, discloses food compositions for beautifying purposes, especially the skin, that are prepared by including collagen and *Centella asiatica*, and/or oceanic deep layer water and optionally amino sugars, ceramides and polyphenols. The agents enhance metabolism of the skin to accelerate the synthesis of collagen and preventing it from deteriorating to keep freshness.

KR 100 846 292 B1 (Intaglio INC), XP002578465, discloses a dispersion type non-aqueous cleansing balm composition for face washing, causes no skin irritation and provides refresh feeling after use. Said dispersion containing at least one polyvalent alcohol (40-75 weight %) chosen from polyalcohol, polyethylene glycol, propylene glycol, glycerin and butylene glycol as solvent, and cleaning agent (5-30 weight %) chosen from sodium cocoyl isethionate, sodium lauryltaurate, sodium laurylglutamate, hydrogenated castor oil, hydrogenated jojoba oil and hydrogenated olive oil. The dispersion further contains scrubbing agent (0.5-15 weight %) chosen from scrub reagent including powdered jojoba wax, apricot stone, grape seed and walnut skin, kaolin and porous zeolite, dispersing agent (01-5 weight %) chosen from poloxamer and hydroxypropylcellulose, and skin irritation-reducing material (001-5 weight %) chosen from carotenoid, astaxanthin, beta-carotene, lycopene, phylloxanthin, proanthocyanidin, flavonoid, riboflavin, vitamin, retinol, ascorbic acid, tocopherol, *Centella asiatica*, bisabolol, chamomile, *Glycyrrhiza uralensis Fisch* and soy isoflavone.

WO 03/080062 (Perrella Segre) discloses compounds for use in sclerotherapy treatment, venous insufficiency, circulation and microcirculation disorders consisting of Folic Acid (vitamin B9), Piridoxine (vitamin B6), Lipoic acid and six different plant extracts: Ginkgo Biloba, Garlic Andrographis, Horse Chestnut, *Centella Asiatica*, and Grape seeds. Sclerotherapy is a procedure used to treat blood vessels or blood vessel malformations (in particular veins) and also those of the lymphatic system. A medicine is injected into the vessels (i.e. veins), which makes them shrink. In conventional sclerotherapy, which is an obliterative procedure, a sclerosing solution is injected exclusively into pathological superficial veins. It is used for children and young adults with vascular or lymphatic malformations. In adults, sclerotherapy is often used to treat varicose veins and hemorrhoids. Another procedure, the so called three-dimensional regenerative sclerotherapy, concerns a regenerative, non-obliterative sclerosing solution which is used in the sclerotherapy of ectatic vessels in the lower limbs. This solution comes into contact with the entire network of superficial and perforating veins.

However there is still a need for an effective and safe composition for the treatment or the prevention of atherosclerosis and in particular atherosclerotic plaques, which therefore especially concerns arteries.

SUMMARY OF THE INVENTION

Applicants have surprisingly found that the combination of Pycnogenol® and *Centella asiatica* extract shows an interesting potential in the treatment of atherosclerosis. This safe natural combination is particularly promising in the treatment and prevention of atherosclerotic plaques especially in arteries.

In one aspect of the present invention there is provided a preparation consisting of the combination of proanthocyanidins (preferably procyanidins) and *Centella asiatica* and/or extracts thereof, in a suitable excipient, for use in the prevention or treatment of atherosclerosis.

In another aspect, the present invention provides for a dietary or food supplement, a food preparation, a beverage, a medicament and a topical preparation comprising the preparation of the present invention.

In a further aspect, the preparation of the present invention is provided for the treatment or the prevention of atherosclerosis which concerns especially arteries.

In a still further aspect, the present invention provides for a method of treating or preventing atherosclerosis, comprising administering to a subject in need thereof an effective amount of the preparation or the medicament of the present invention.

DETAILED DESCRIPTION OF THE INVENTION

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components.

As used in the specification and claims, the singular form "a", "an" and "the" include plural references unless the context clearly dictates otherwise.

As used herein the term "pine bark extract" refers to a French maritime pine bark extract which is, for example, commercially available as Pycnogenol® (Horphag). The terms "Pycnogenol®", "pine bark extract" and "French maritime pine bark extract" are interchangeable. *Pinus pinaster* (*P. pinaster*) and *Pinus maritima* (*P. maritime*), are understood to refer to the same organism commonly called "French Maritime Pine." Hence, these terms are interchangeable.

The term "extract", as used herein includes any preparation obtained from plants, fruits or vegetables using an extraction method.

The term "food preparation" refers generally to material of either plant or animal origin, or of synthetic sources, that contain essential nutrients such as a carbohydrate, protein, fat, vitamin, mineral, etc. used in the body of an organism to sustain growth, repair, and vital processes and to furnish energy A "dietary or food supplement" refers to a product that contains substances like vitamins, minerals, foods, botanicals, amino acids and is intended to supplement the usual intake of these substances. Dietary supplements are found in pill, tablet, capsule, powder or liquid form and are meant to be taken by mouth.

The term "nutraceutical" refers to any substance that is a food or a part of a food and provides medical or health benefits, including the prevention and treatment of disease. Such products may range from isolated nutrients, dietary supplements and specific diets to genetically engineered designer foods, herbal products, and processed foods such as cereals, soups and beverages. It also refers to a product isolated or purified from foods, and generally sold in medicinal forms not usually associated with food and demonstrated to have a physiological benefit or provide protection against diseases like chronic diseases for example.

The term "beverage" means a liquid for drinking, which may be water, flavored water, soft drinks, alcoholic drink, health drink, or an enriched drink like based on a diary product (milk) or fruit juice.

"Pharmaceutically acceptable excipients or carriers" are any materials that do not interfere with the pharmacological activity of the active ingredient(s) or degrade the body functions of the subject to which it can be administered but facilitate fabrication of dosage forms or administration of the composition. Examples of pharmaceutically acceptable excipient include but are not limited to maltodextrin, calcium phosphate, and fused silica. Pharmaceutically acceptable excipients also include flavorants, as well as various additives such as other vitamins and minerals, all solvents, dispersion media, coatings, isotonic and absorption delaying agents, sweeteners and the like, non-toxic auxiliary substances such as wetting or emulsifying agents, pH buffering agents and the like, such as for example, sodium acetate, sorbitan monolaurate, triethanolamine oleate, and inert ingredients such as talc and magnesium stearate which are standard excipients in the manufacture of tablets, capsules and other dosage forms.

As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject. The term does not denote a particular age or sex. Thus, adult and newborn subjects, whether male or female, are intended to be covered.

The term "an effective amount" refers to an amount necessary to obtain a physiological effect. The physiological effect may be achieved by one application dose or by repeated applications. The dosage administered may, of course, vary depending upon known factors, such as the physiological characteristics of the particular composition; the age, health and weight of the subject; the nature and extent of the symptoms; the kind of concurrent treatment; the frequency of treatment; and the effect desired and can be adjusted by a person skilled in the art.

The term "TTFCA" refers to the total triterpenic fraction of *Centella asiatica*.

"Atherosclerosis" is a process of progressive thickening and hardening of the walls of medium-sized and large arteries as a result of fat deposits on their inner lining.

In other words, Atherosclerosis (also known as arteriosclerotic vascular disease or ASVD) is a condition in which an artery wall thickens as the result of a build-up of fatty materials such as cholesterol. It is a syndrome affecting arterial blood vessels, a chronic inflammatory response in the walls of arteries, in large part due to the accumulation of macrophage white blood cells and promoted by low-density lipoproteins (plasma proteins that carry cholesterol and triglycerides) without adequate removal of fats and cholesterol from the macrophages by functional high density lipoproteins (HDL). It is commonly referred to as a hardening or furring of the arteries. It is caused by the formation of multiple plaques within the arteries (see: http://en.wikipedia.org/wiki/Atherosclerosis).

Applicants have studied specific plants and their potential application in the treatment of atherosclerosis. Surprisingly it was found that the administration of a preparation consisting of the combination of proanthocyanidins (preferably procyanidins) and *Centella asiatica* and/or extracts thereof, in a suitable excipient, considerably reduces the atherosclerosis risks. Indeed, the preparation of the present invention—of completely natural origin—stops the progression of atherosclerosis from subclinical to clinical stages in several patients. The synergy action of a composition comprising proanthocyanidins and a composition comprising *Centella asiatica* and/or extracts thereof seems to be separated by any other pharmacological action (i.e. cholesterol lowering, antihypertensive, antiplatelets) (see the Example).

Proanthocyanidins designates a group of flavonoids that includes the subgroups procyanidins, prodelphinidins and propelargonidins. Proanthocyanidins are homogeneous or heterogeneous polymers consisting of the monomer units catechin or epicatechin, which are connected either by 4-8 or 4-6 linkages, to the effect that a great number of isomer proanthocyanidins exist. Typically, the proanthocyanidins oligomers have a chain length of 2-12 monomer units. Proanthocyanidins may be synthesized or extracted from a plant material. Non-limiting examples of plant material sources of proanthocyanidins include grape seeds, grape skin, pine barks, ginkgo leaves, peanuts, cocoa beans, tamarind, tomato, peanut, almond, apple, cranberry, blueberry, tea leaves.

A well-known product containing proanthocyanidins, which is available in trade as a preparation of a food supplement under the name Pycnogenol®, is an extract of the French maritime pine bark (*Pinus pinaster*), see also U.S. Pat. No. 3,436,407 (MASQUELIER JACQUES); U.S. Pat. No. 5,720,956 (ROHDEWALD, PETER) and U.S. Pat. No. 6,372,266 (SUZUKI NOBUTAKA et al. Horphag Research Ltd.) which are incorporated herein by reference. Pycnogenol® is a standardized bark extract of the French maritime pine *Pinus pinaster*, Aiton, subspecies Atlantica des Villar. The quality of this extract is specified in the United States Pharmacopeia (USP 28) (Maritime Pine Extract. In: United States Pharmacopeia. Rockville: United States Pharmacopeial Convention, Inc.; 2005. pp 2115-2116). The extract consists of a concentrate of polyphenols, which are also contained in fruits and vegetables, but, in low concentrations. The polyphenols are composed from flavonoids, especially procyanidins, and phenolic acids. All these constituents possess the ability to inactivate free radicals. Rohdewald P. A review of the French maritime pine bark extract (Pycnogenol®), a herbal medication with a diverse pharmacology. Int J Clin Pharmacol Ther 2002; 40(4): 158-168. Between 65-75% of Pycnogenol® are procyanidins comprising of catechin and epicatechin subunits with varying chain lengths (Rohdewald P. A review of the French maritime pine bark extract (Pycnogenol®), an herbal medication with a diverse clinical pharmacology. Int J Clin Pharmacol Ther 2002; 40: 158-168). Other constituents are polyphenolic monomers, phenolic or cinnamic acids and their glycosides (Id.). Pycnogenol® extract is standardized to contain between 65% and 75% procyanidins (70+/−5% procyanidins) in compliance with USP 28, compounds known for relatively significant antioxidant and anti-inflammatory activity, among other actions (Rohdewald P. "Pycnogenol®, French Maritime Pine Bark extract", Encyclopedia of Dietary Supplements, 2005, pp 545-553).

*Centella asiatica* is a small herbaceous annual plant used in a number of cosmetics application and health remedies. It is a member of the Mackinlayaceae family (Apiaceae) or Mackinlayoideae subfamily, and is native of Sri Lanka, northern Australia, Indonesia, Iran, Malaysia, Melanesia, New Guinea, and other parts of Asia. It is also commonly named gotu kola, Asiatic Pennywort, Indian Pennywort, Luei Gong Gen, Takip-kohol, Antanan, Pegagan, Pegaga, vallaarai, Kula laid, Bai Bua Bok, Brahmi and rau má. *Centella asiatica* is also currently used in its countries of origin in culinary preparations as accompaniment or as a drink.

*Centella asiatica* extract consists of the leaves and roots of the hydrocotyle *centella asiatica*. The main active ingredients contained in *centella asiatica* are triterpenoids asiatic acid, madecassic acid, asiaticoside (triterpenoid ester glycosides), inadecassoside, and brahminoside. A volatile oil comprising p-cymol, b-caryophyllene and farnesene is also found in the plant. Extracts of *Centella asiatica* are also commercially available. Alternatively, *Centella asiatica* extracts can be prepared from the plant *Centella asiatica* by extraction techniques such as are well known in the art, including extractions in hydrophobic and hydrophilic solvents.

The present invention provides for a preparation consisting of the combination of proanthocyanidins (preferably procyanidins) and *Centella asiatica* and/or extracts thereof, in a suitable excipient, for use in the prevention or treatment of atherosclerosis. The preparation of the present invention contains from 20% to 80% w/w of proanthocyanidins (preferably procyanidins) and from 20% to 80% w/w respectively of *Centella asiatica* and/or extracts thereof and a suitable excipient q.s.p. (quantity sufficient per 100% of the total volume). Preferably, the preparation of the invention comprises about 30% to 70% w/w of proanthocyanidins (preferably procyanidins) and from 30% to 70% w/w respectively of *Centella asiatica* and/or extracts thereof, more preferably about 40% to 60% w/w of proanthocyanidins (preferably procyanidins) and respectively 40% to 60% w/w of *Centella asiatica* and even more preferably about 50% w/w of proanthocyanidins (preferably procyanidins) and respectively 50% w/w of *Centella asiatica* and a suitable excipient q.s.p. According to the example, the preparation of the invention comprises the combination of Pycnogenol® and TTFCA (with or without Aspirin) (tablets, 100 mg for each component). Pycnogenol® extract is standardized to contain between 65% and 75% of proanthocyanidins, preferably procyanidins (70+/−5% procyanidins). Thus tablets used in the example contain 100 mg of TTFCA and between 65 mg and 75 mg of proanthocyanidins, preferably 65 mg and 75 mg of procyanidins.

The preparation of the invention comprises proanthocyanidins preferably consisting of procyanidins originated from a plant extract or from a synthesized material (i.e., synthetic proanthocyanidins).

The plant extract can be selected from the group consisting of proanthocyanidins containing extracts selected among extracts of pine bark, the cones of cypresses grape seed, apples, peanut skin, walnuts, pomegranates, tomatoes, almonds, tea, hawthorn, cocoa or combination thereof. Proanthocyanidins containing rich extracts are natural and preferably plant extracts having more than 50% by weight (of dried extracts) of proanthocyanidins, more preferably more than 70% by weight and even more preferably more than 75% by weight of proanthocyanidins (preferably procyanidins). Preferably the plant extract according to the present invention is originated from pine bark and more preferably the plant extract is Pycnogenol®.

In a preferred embodiment, the preparation comprising proanthocyanidins may be a pine bark extract. The pine bark may be from *P. pinaster*, such as, for example, from Pycnogenol®. In a preferred embodiment, the composition may contain proanthocyanidins at a concentration of 10% to 100% of total weight. For example, a Pycnogenol® composition may be diluted or concentrated to contain 10%, 20%, 30%, 40%, 50%, 60%, 70%, 75%, 80%, 90% or 95% proanthocyanidins (preferably procyanidins). Concentration may be performed using known methods such as column chromatography or affinity chromatography.

In a preferred embodiment, *Centella asiatica* extracts, present in the preparation of the invention, are the total triterpenic fraction of *Centella asiatica* (TTFCA).

Examples of suitable excipients of this invention include, but are not limited to, anti-adherents, binders (e.g., macrocrystalline cellulose, gum tragacanth, or gelatin), coatings, disintegrants, fillers, diluents, softeners, emulsifiers, flavoring agents, coloring agents, adjuvants, lubricants, functional agents (e.g., nutrients), viscosity modifiers, bulking agents, glidiants (e.g., colloidal silicon dioxide) surface active agents, osmotic agents, diluents, or any other non-active ingredient, or combinations thereof.

For example, the preparation of the present invention may include excipient materials selected from the group consisting of calcium carbonate, coloring agents, whiteners, preservatives, and flavors, triacetin, magnesium stearate, sterotes, natural or artificial flavors, essential oils, plant extracts, fruit essences, gelatins, or combinations thereof.

Optionally the preparation of the present invention may include other artificial or natural sweeteners, bulk sweeteners, or combinations thereof. Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and combinations thereof.

The suitable excipient can be also a pharmaceutically acceptable excipient.

Optionally the preparation of the present invention can further comprise a non-steroidal anti-inflammatory drug such as acetylsalicylic acid (aspirin).

The present invention further provides for a food preparation, a dietary or food supplement, a nutraceutical, a beverage, a medicament and a topical preparation comprising the preparation of the present invention. As described above, the medicament and the topical preparation may further comprise acetylsalicylic acid (aspirin) as well as a pharmaceutically acceptable excipient.

Preferably, the dietary supplement, the nutraceutical or the medicament of the present invention is administered at a dosage of between 5 mg per day to 2,000 mg per day. Preferably between 50 mg to 1,000 mg per day and even more preferably between 100 mg to 400 mg per day. The dietary supplement, the nutraceutical or the medicament of the present invention contains from 20% to 80% w/w of proanthocyanidins (preferably procyanidins) and from 20% to 80% w/w respectively of *Centella asiatica* and/or extracts thereof and a suitable excipient q.s.p. It is known that Pycnogenol® extract is standardized to contain between 65% and 75% of proanthocyanidins, preferably procyanidins. Therefore, tablets used in the example do contain 100 mg of TTFCA TECA and between 65 mg and 75 mg of proanthocyanidins, preferably 65 mg and 75 mg of procyanidins, more preferably 70 mg of proanthocyanidins or procyanidins.

The present invention further provides the preparation of the invention for use in the treatment or the prevention of atherosclerosis which concerns especially arteries. Preferably said treatment or prevention concerns atherosclerotic plaques.

The present invention also provides for a method of treating or preventing atherosclerosis disorders comprising administering to a subject in need thereof an effective amount of the preparation or of the medicament of the present invention. Said atherosclerosis disorders are preferably atherosclerotic plaques and said subject is a mammal, preferably a human.

The preparation, the dietary supplement, the nutraceutical or the medicament of the present invention can be administered orally, parenterally or topically at a dosage of between 5 mg per day to 2,000 mg per day. Preferably between 50 mg to 1,000 mg per day and more preferably between 100 mg to 400 mg per day. The concentrations of the active ingredients in the preparation are described above.

If intended for oral administration, the medicament of the present invention can be in the form, for example, of a tablet, a caplet, a pill, a hard or soft capsule, a lozenge, a cachet, a dispensable powder, granules, a suspension, an elixir, a dispersion, a liquid, or any other form reasonably adapted for such administration. If intended for parenteral administration, it can be in the form, for example, of a solution for intravenous, intramuscular or subcutaneous injection.

The topical preparations according to the present invention can be, but not limited to, a cream, a patch, a gel, an ointment, a lotion, a tincture, a spray, a mousse, a cleansing composition or a foam. The topical preparations of the present invention can be also in the form of a suspension or dispersion in solvents or fatty substances, or alternatively in the form of an emulsion or micro emulsion, PET-emulsions, multiple emulsions, bickering emulsions, hydrogels, alcoholic gels, lipogels, one or multiphase solutions or a vesicular dispersion and other usual compositions, which can also be applied by pens, as masks or as sprays. The emulsions can also contain anionic, nonionic, cationic or amphoteric surfactant(s).

In a preferred embodiment, the preparation according to the invention comprises proanthocyanidins (preferably procyanidins) and *Centella asiatica* and/or extracts thereof as the sole active ingredients administered to a subject.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practising the present invention and are not intended to limit the scope of the invention.

Examples

Variation in echogenicity of echolucent carotid and femoral atherosclerotic plaques with combined treatment (Pycnogenol 100 mg+TTFCA 100 mg, with or without Aspirin 100 mg). A prospective, pilot 6-month trial.

(TTFCA=total triterpenic fraction of *Centella asiatica*)

This study has evaluated whether a combination of Pycnogenol® and TTFCA, with or without Aspirin, was effective in reducing plaque progression and cardiovascular risk of events by decreasing platelet aggregation, local arterial inflammation and the intima-media scarring process due to inflammation at the level of carotid and femoral arteries bifurcations.

The reduction in risk of cardiovascular events should have been obtained—by the study hypothesis—by modulating collagen production in plaques mainly by producing a visible increase (ultrasound) in echogenicity in echolucent (soft, black on ultrasound, prone to embolisation and thrombosis causing events) femoral and carotid plaques.

This prospective placebo-controlled trial had the purpose of evaluating the effects of Pycnogenol® and TTFCA, with or without Aspirin, selectivity on hypoechoic-echolucent plaques.

The sonographic examination of carotid plaques was made with high-resolution ultrasound.

Capturing plaques images, digital image processing, and normalization were standardized. The interobserver, intrascanner, gain-level variability were also standardized using as reference blood (black) for the most echolucent parts of the plaque and the adventitia (white) as the most echogenic part. The technique for plaque characterization and GSM (Grey Scale Median) measurements had been previously described in details.

In previous studies, after the ultrasonic plaque area had been obtained, normalization of echo texture had been obtained and plaque characterization had been used to differentiate echo-texture of plaque associated with cardiovascular events and those that did not cause embolization, thrombosis, or cardiovascular events (i.e. TIAs, strokes, embolisation, thrombosis).

In this study, after identifying plaques at higher risk (black, "soft", echolucent plaques), patients were treated with the combination Pycnogenol® and TTFCA (with or without Aspirin) (tablets, 100 mg for each component) once daily for 6 months to evaluate whether this aggregate compound, by its antiplatelet action, anti-inflammatory effects and by modulating local collagen synthesis, could increase the echogenicity and therefore the stability of echolucent plaques. No other treatment was used during the 6 months follow-up.

Asymptomatic patients with carotid/femoral bifurcation, irregular, echolucent plaques (GSM<18) causing >65% stenosis (on duplex) were treated with Pycnogenol® and TTFCA (with or without Aspirin) or with comparable placebo after informed consent.

All patients (including controls) were treated with antiplatelet agents (in the group of interest the antiplatelet action was obtained by the combined activity of Aspirin and Pycnogenol®). This association may have a combined anti-aggregating effect possibly comparable to 400 mg of Aspirin (which could be not tolerated in most patients). The details of groups are shown in Table 1 and Table 2.

RESULTS: At inclusion the GSM in the hypoechoic plaques treatment group was 15.1 (range, 11-17.4); at 6 months GSM was increased (the increase was significant as GSM raised to 19.5; SD 1.1; P<0.05). There was no change in GSM in the comparable controls.

In conclusion the observed results suggest an important positive action of the combination of Pycnogenol®+TTFCA and the combination Pycnogenol®+TTFCA+Aspirin (APT) on the stabilization of hypoechoic, low-density (soft) carotid and femoral plaques which are the most dangerous types of plaques, associated to cardiovascular events due to embolisation of thrombosis.

The preparation of the present invention—of completely natural origin—stops the progression of atherosclerosis from subclinical to clinical stages in several patients. The synergy action of Pycnogenol® and TTFCA (with or without Aspirin) seems to be separated by any other pharmacological action (i.e. cholesterol lowering, anti-hypertensive, antiplatelets).

TABLE 1

|  | AGE | Number of patients | Males | Plaques Femoral | Plaques Carotid |
|---|---|---|---|---|---|
| APT PATIENTS | 63.3; 7 | 57 | 38 | 66 | 69 |
| CONTROLS | 62.4; 5.1 | 58 | 34 | 57 | 66 |

TABLE 2

GSM Measurement

| Treatment | GSM at baseline | At 6 months* |
|---|---|---|
| Pycnogenol 100 mg/day + *Centella* 100 mg/day | 15.2; SD 2.3 | 17/20** |
| Pycnogenol 100 mg/day + *Centella* 100 mg/day + Aspirin 100 mg/day | 15.1; SD 2.1 | 19/20** |
| Pycnogenol ® Group 100 mg/day | 15.0; SD 2.9 | 3/18** |

TABLE 2-continued

GSM Measurement

| Treatment | GSM at baseline | At 6 months* |
|---|---|---|
| Centella Group 100 mg/day | 14.9; SD 3.0 | 8/18** |
| Aspirin Group | 15.3; SD 3.1 | 2/18 |
| Untreated Group (Control) | 15.2; SD 2.8 | 0/18 |

**Indicates significant change both from initial value and in comparison with control
*Number of patients with an increase of plaques Grey Scale Median of at least 5 points.

The invention claimed is:

1. A method of treating atherosclerosis, comprising:
    administering to a subject, having atherosclerosic plaques, an effective amount of a preparation comprising, in a suitable excipient, a combination of:
    a French maritime pine bark extract standardized to contain between 65% and 75% of proanthocyanidins, and
    a total triterpenic fraction of *Centella asiatica,*
    wherein said combination consists of the French maritime pine bark extract and the total triterpenic fraction of *Centella asiatica* in a 1:1 w/w ratio.

2. The method according to claim 1, wherein said preparation further comprises acetylsalicylic acid.

3. The method according to claim 1, wherein the suitable excipient is a pharmaceutically acceptable excipient.

4. The method according to claim 1, wherein the preparation is administered to the subject in the form of a food preparation.

5. The method according to claim 1, wherein the preparation is administered to the subject in the form of a dietary supplement.

6. The method according to claim 1, wherein the preparation is administered to the subject in the form of a nutraceutical.

7. The method according to claim 1, wherein the preparation is administered to the subject in the form of a beverage.

8. The method according to claim 1, wherein the preparation is administered to the subject in the form of a medicament.

9. The method according to claim 1, wherein the preparation is administered to the subject in the form of a topical preparation.

10. The method according to claim 1, wherein the preparation is administered orally, parenterally or topically.

11. The method according to claim 1, wherein the subject is one of a mammal and a human.

12. A method of treating atherosclerosic plaques in arteries, comprising:
    administering to a subject, having the atherosclerosic plaques in arteries, an effective amount of a preparation comprising, in a suitable excipient, a combination of:
    a French maritime pine bark extract standardized to contain between 65% and 75% of proanthocyanidins, and
    a total triterpenic fraction of *Centella asiatica,*
    wherein said combination consists of the French maritime pine bark extract and the total triterpenic fraction of the *Centella asiatica* in a 1:1 w/w ratio.

* * * * *